United States Patent
Peng et al.

(10) Patent No.: US 12,060,369 B2
(45) Date of Patent: Aug. 13, 2024

(54) ORGANIC ELETROLUMINESCENT MATERIAL, PREPARATION METHOD THEREOF AND ORGANIC ELETROLUMINESCENT DEVICE

(71) Applicant: GUANGDONG AGLAIA OPTOELECTRONIC MATERIALS CO., LTD, Guangdong (CN)

(72) Inventors: Jiahuan Peng, Foshan (CN); Huiyang Li, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 591 days.

(21) Appl. No.: 17/297,876

(22) PCT Filed: Nov. 2, 2019

(86) PCT No.: PCT/CN2019/115178
§ 371 (c)(1),
(2) Date: May 27, 2021

(87) PCT Pub. No.: WO2020/125239
PCT Pub. Date: Jun. 25, 2020

(65) Prior Publication Data
US 2022/0033421 A1    Feb. 3, 2022

(30) Foreign Application Priority Data
Dec. 17, 2018 (CN) .......................... 201811544417.9

(51) Int. Cl.
| | | |
|---|---|---|
| *C07D 519/00* | (2006.01) | |
| *C07D 405/14* | (2006.01) | |
| *C07D 487/14* | (2006.01) | |
| *C07D 513/04* | (2006.01) | |
| *H10K 85/60* | (2023.01) | |
| *H10K 50/11* | (2023.01) | |
| *H10K 71/00* | (2023.01) | |
| *H10K 71/12* | (2023.01) | |
| *H10K 101/10* | (2023.01) | |

(52) U.S. Cl.
CPC ......... *C07D 519/00* (2013.01); *C07D 405/14* (2013.01); *C07D 487/14* (2013.01); *C07D 513/04* (2013.01); *H10K 85/615* (2023.02); *H10K 85/631* (2023.02); *H10K 85/6572* (2023.02); *H10K 85/6574* (2023.02); *H10K 85/6576* (2023.02); *H10K 50/11* (2023.02); *H10K 71/00* (2023.02); *H10K 71/12* (2023.02); *H10K 2101/10* (2023.02)

(58) Field of Classification Search
None
See application file for complete search history.

(56) References Cited

FOREIGN PATENT DOCUMENTS

| CN | 1701111 A | 11/2005 |
|---|---|---|
| CN | 107827913 A | 3/2018 |

OTHER PUBLICATIONS

Tan Zhenda et al., "Aerobic Copper-Catalyzed Halocyclization of Methyl N-Heteroaromatics with Aliphatic Amines: Access to Functionalized Imidazo-Fused N-Heterocycles", J. Org. Chem. (Oct. 3, 2016).
Qian Peng et al., "Electrocatalytic Intermolecular C(sp3)—H/N—H Coupling of Methyl N-Heteroaromatics with Amines and Amino Acids: Access to Imidazo-Fused N-Heterocycles", Org. Lett. (Oct. 3, 2018).

*Primary Examiner* — Robert S Loewe
(74) *Attorney, Agent, or Firm* — Maschoff Brennan

(57) ABSTRACT

The invention provides an organic electroluminescent material, preparation method thereof and an organic electroluminescent device. The organic electroluminescent material of the invention is a class of compounds based on imidazole[1,5-a][1,8]naphthyridine, and has a structure presented by Formula (I) as below. The invention also provides application of the material in organic light-emitting diodes (OLED). The compound of the invention has high stability, and the organic electroluminescent device according to the invention has high efficiency.

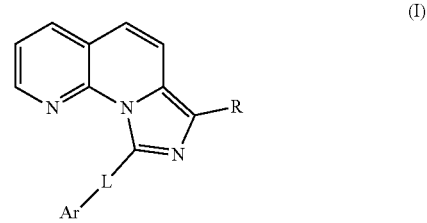

(I)

17 Claims, 2 Drawing Sheets

ORGANIC ELETROLUMINESCENT MATERIAL, PREPARATION METHOD THEREOF AND ORGANIC ELETROLUMINESCENT DEVICE

FIELD OF THE INVENTION

The invention relates to the field of organic electroluminescent materials, in particular to a compound based on imidazole[1,5-a][1,8]naphthyridine, and also relates to a light-emitting device.

BACKGROUND

OLED is namely an organic light-emitting diode or an organic light-emitting device. OLED is an independent light-emitting device without backlight, has characteristics such as fast response speed, low driving voltage, high light-emitting efficiency, high resolution, and wide viewing angle, so it has already become a new generation of display and lighting technologies, especially with huge application prospects in mobile phones, computers, TVs, bendable and foldable electronic products.

There are currently two types of light-emitting material used in OLEDs: fluorescent materials and phosphorescent materials. The light-emitting materials used in early devices are mainly organic small-molecule fluorescent materials, and spin statistics quantum theory shows that the theoretical internal quantum efficiency of fluorescent materials is only 25%. In 1998, Professor Forrest of the Princeton University and Professor Thompson of the University of Southern California discovered the phosphorescent electroluminescence of metal organic complex molecular materials at room temperature. The strong spin-orbit coupling of heavy metal atoms can effectively promote the intersystem crossing (ISC) of electrons from singlet to triplet, so that OLED devices can make full use of the singlet and triplet excitons generated by electrical excitation to make the theoretical internal quantum efficiency of light-emitting material reach 100% (Nature, 1998, 395, 151).

In OLED materials, as organic electroluminescent materials mostly transport holes at a speed one or two orders of magnitude greater than the speed of transporting electrons, it is easy to cause an imbalance in the number of electrons and holes in the light-emitting layer, resulting in relatively low efficiency of the obtained device. Therefore, selecting and optimizing the subject material in the light-emitting layer has a great impact on improving the efficiency and lifetime of the organic electroluminescent device. Since inventing CBP, it has been widely used in the light-emitting layer of phosphorescent devices. Although the carbazole group induces CBP to have a higher triplet energy level and can be used in the light-emitting layer of phosphorescent materials, it is mainly a hole-transporting material, which has a low speed for transporting electrons, so it is easy to cause carrier injection and unbalanced transmission. In addition, the glass transition temperature Tg of CBP is relatively low, which is not conducive to the stable use of the device. Therefore, developing subject materials for the light-emitting layer with high stability and balanced carrier transport is of great value for the widespread use of organic electroluminescent devices.

SUMMARY

The invention provides a compound based on imidazole [1,5-a] [1,8]naphthyridine, which has good thermal stability and high capability of balanced hole/electron transport. The invention also provides the application of the material in organic light emitting diodes (OLED), and the device manufactured by using the organic electroluminescent compound has the advantages such as good electroluminescence efficiency, excellent color purity and long life span.

An organic electroluminescent material has a compound with the structure of Formula (I):

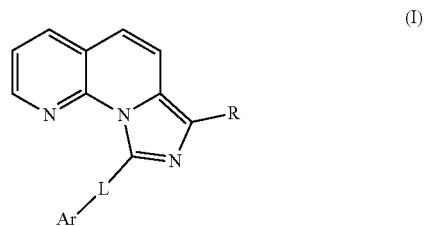

(I)

Where Ar is selected from a C6-C30 substituted or unsubstituted aryl group, a C5-C30 substituted or unsubstituted aryl group having one or more heteroatoms, a N-aryl substituted carbazolyl group, a N-aryl substituted indenocarbazole derivative substituent group, a diarylamino group or a $R_1$-$R_8$ substituted diarylamino group and cyclic derivatives thereof Cy. Z is $C(R_9)_2$, $Si(R_9)_2$, O, S, $NR_9$ or $SO_2$. Wherein $R_1$-$R_9$ are independently a hydrogen atom, a deuterium atom, halogen, an unsubstituted alkyl group, a halogenated alkyl group, a deuterated alkyl, a cycloalkyl, an unsubstituted aryl, an alkyl-substituted aryl, an alkoxyl group, a cyano group, a carbazolyl group or a diphenylamine group, or $R_1$-$R_9$ independently form a 5-8 membered ring with adjacent groups. Cy:

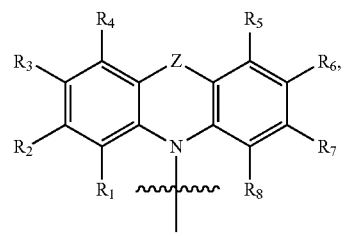

L is selected from a phenylene group, a biphenylene group or a naphthalene group.

R is selected from a hydrogen atom, a deuterium atom, a C6-C10 substituted or unsubstituted aryl group or a C6-C10 heteroaryl group.

Ar is selected from a phenyl group, a naphthyl group, a biphenyl group, a phenanthryl group, an anthracenyl group, an arylanthryl group, a pyrenyl group, a dibenzofuranyl group, a dibenzothienyl group, a benzimidazolyl group, a pyridyl group, a pyrimidinyl group, a quinolyl group, an isoquinolyl group, a triazinyl group, a pyrrolyl group, a furanyl group, a thiazolyl group, a quinazolinyl group, a triazolyl group, a benzothiazolyl group, a benzothiadiazolyl group, a 1,2,4-triazolyl group, a triphenylamino group, an arylcarbazolyl group, a N-aryl substituted carbazolyl group, a diphenylamino group, an acridinyl and derivative thereof substituent group, a phenoxazinyl and derivative thereof substituent group or a phenothiazinyl and derivative thereof substituent group. R is selected from a hydrogen atom, a phenyl group, a naphthyl group or a pyridyl group.

Preferably, Ar is selected from a phenyl group, a naphthyl group, a biphenyl group, a phenanthryl group, an anthracenyl group, an arylanthryl group, a pyrenyl group, a dibenzofuranyl group, a dibenzothienyl group, a benzimidazolyl group, a pyrimidinyl group, a triazinyl group, a quinazolinyl group, a 1,2,4-triazolyl group, a N-phenyl-carbazole group or an acridinyl and derivative thereof substituent group.

Some specific non-limiting examples of the complexes has Formula (I) are as below:

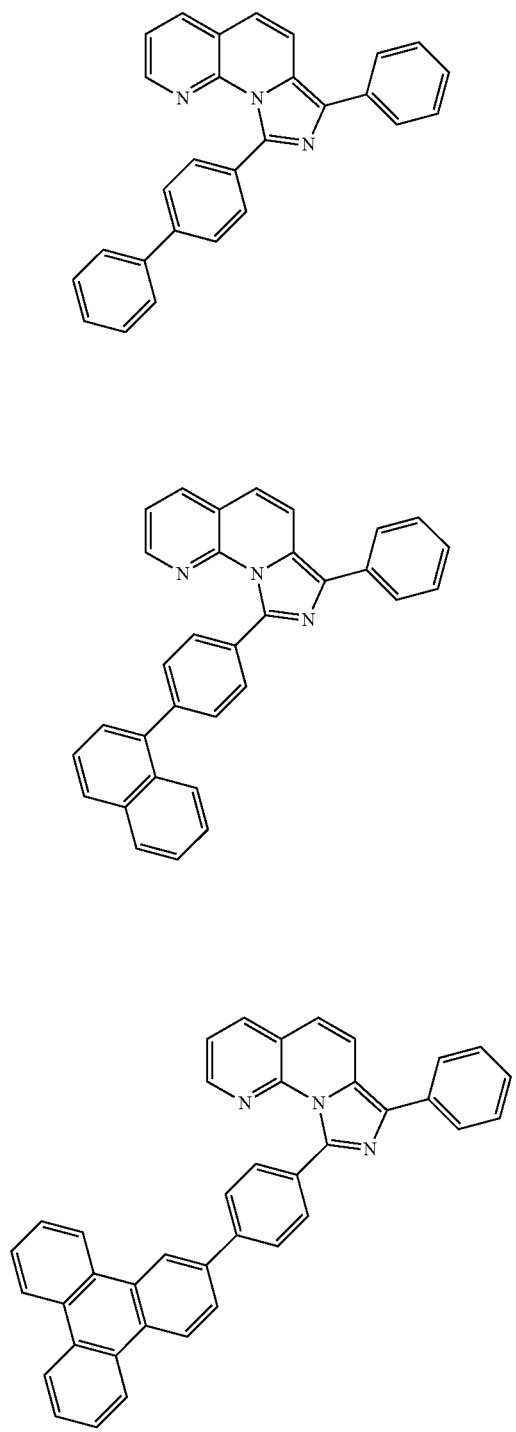

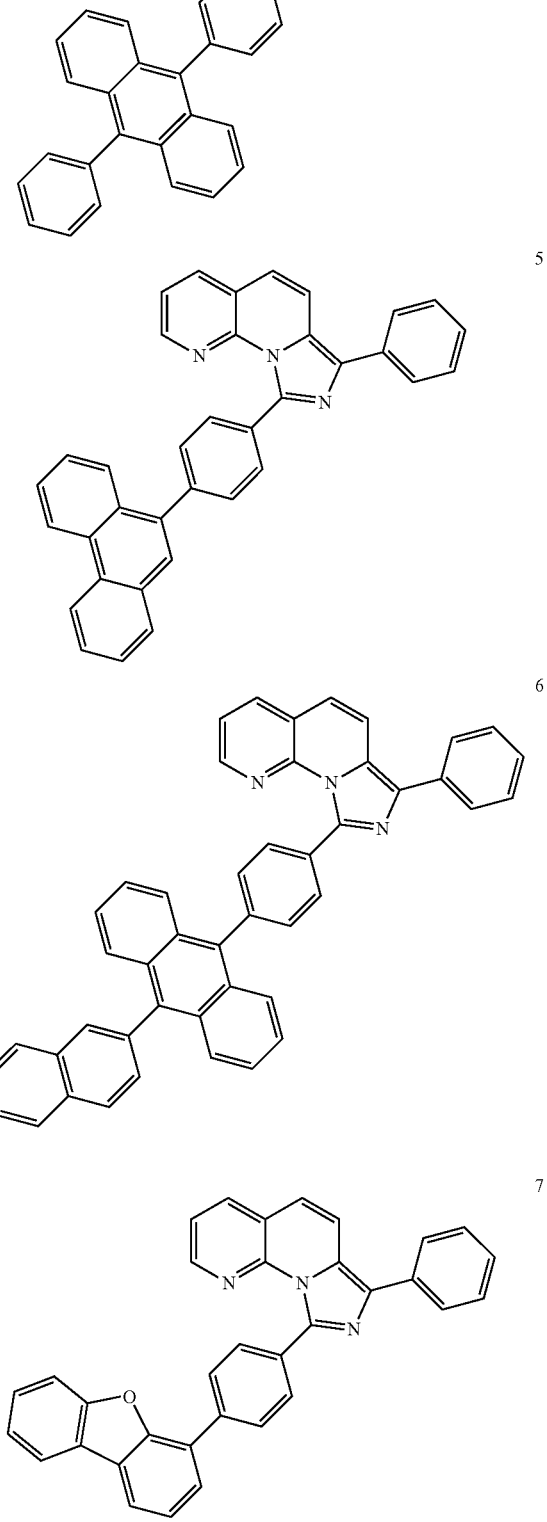

8
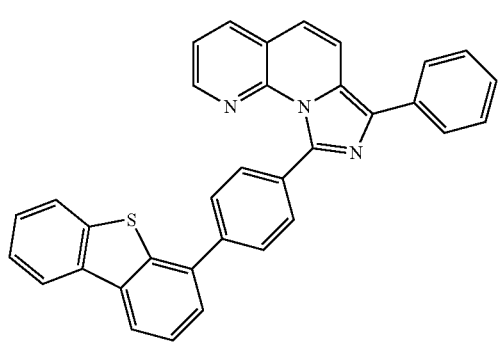
9
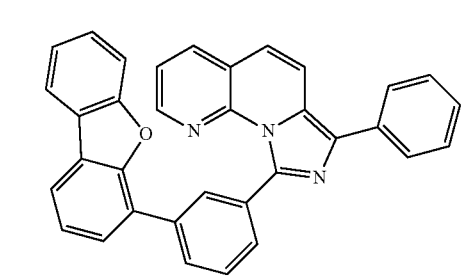
10
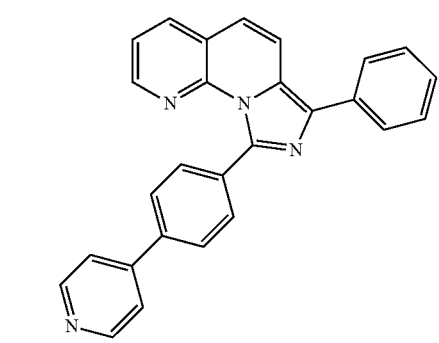
11
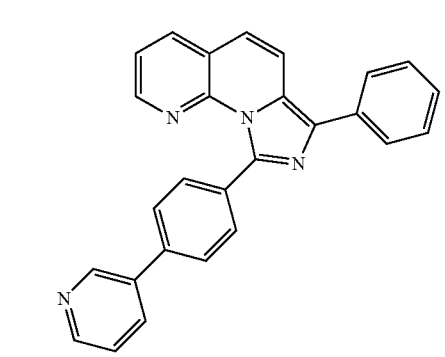
12
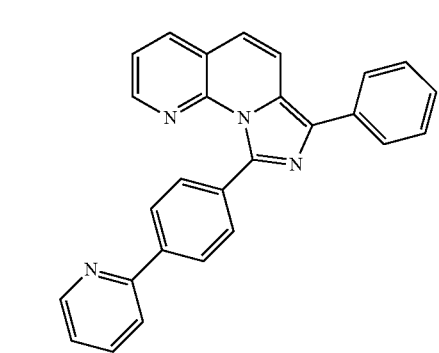
13
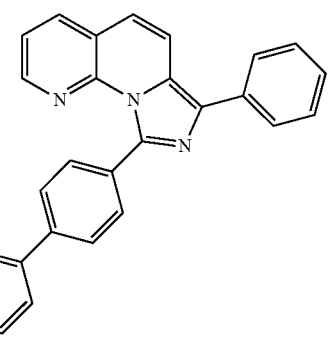
14
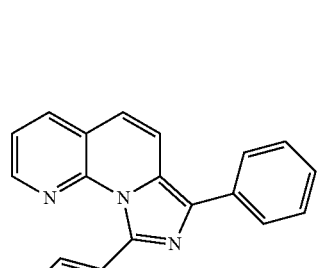
15
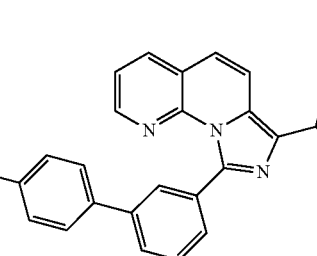
16
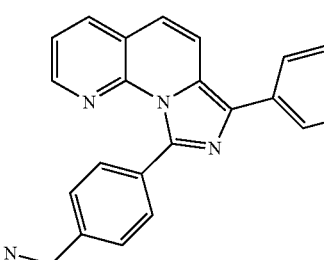

-continued
17
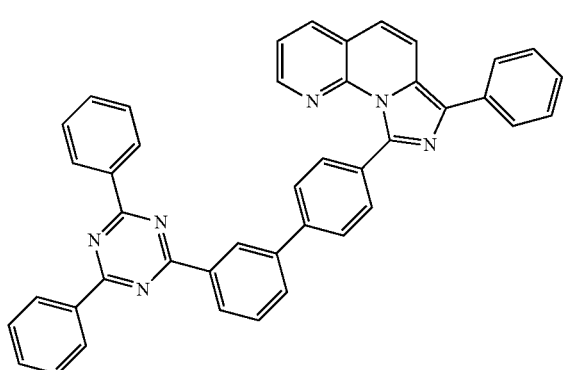
18
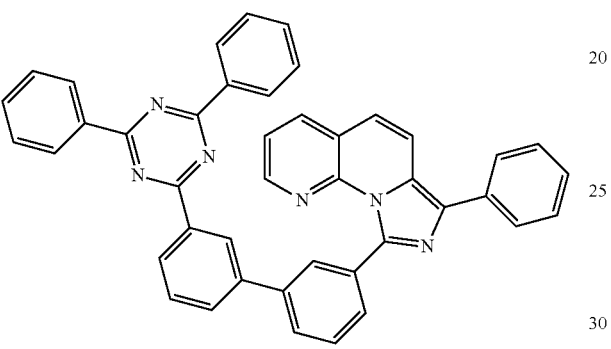
19
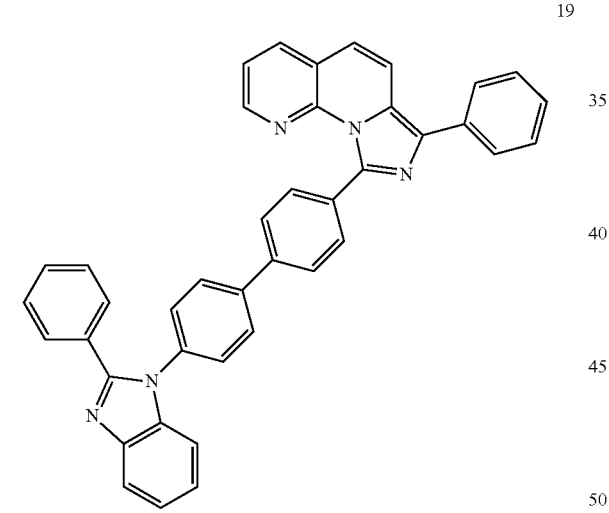
20
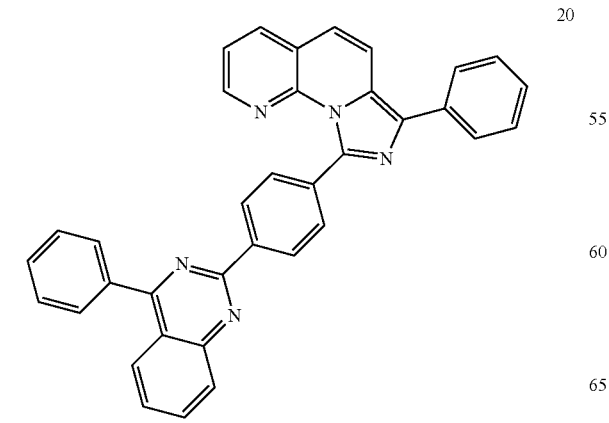
-continued
21
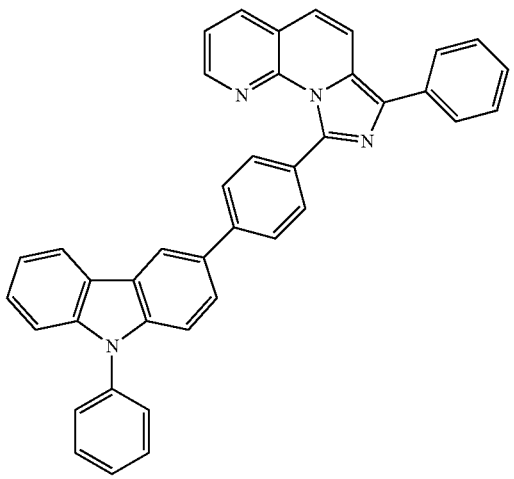
22
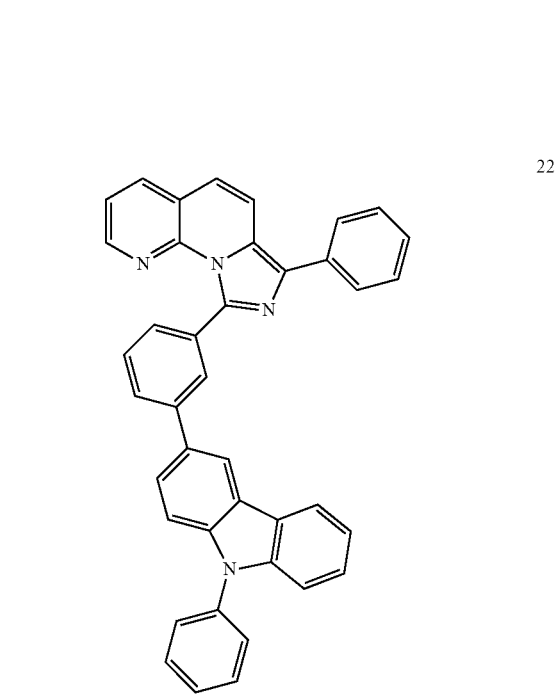
23
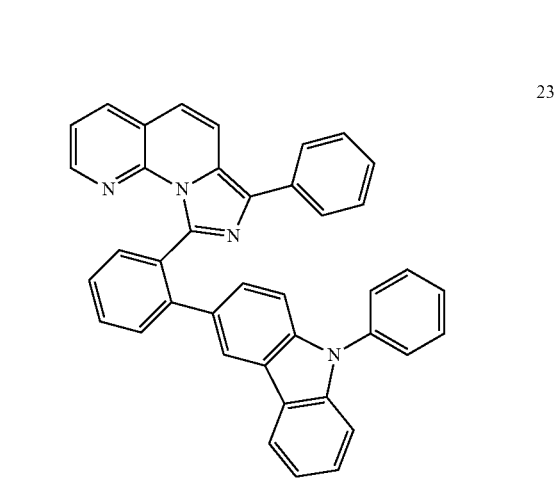

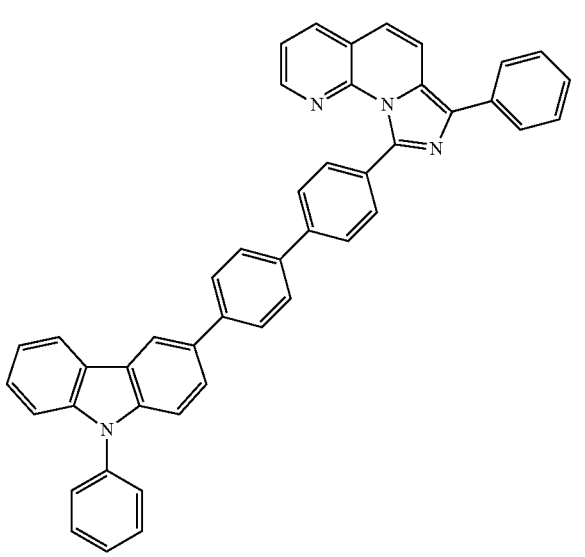
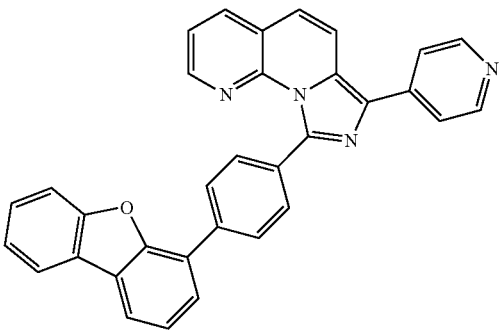
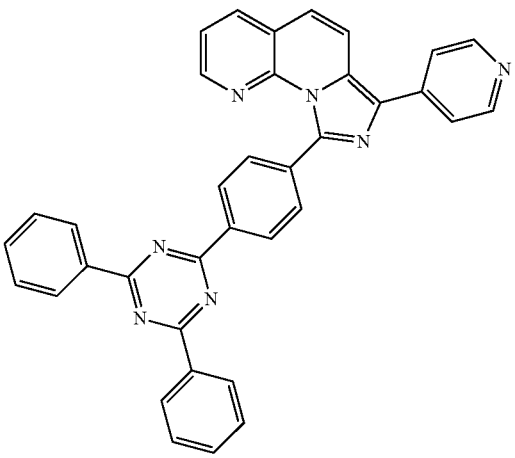
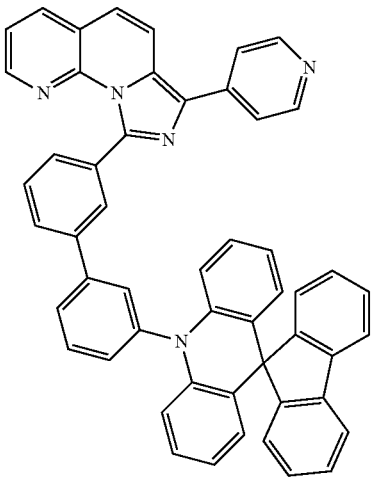

-continued
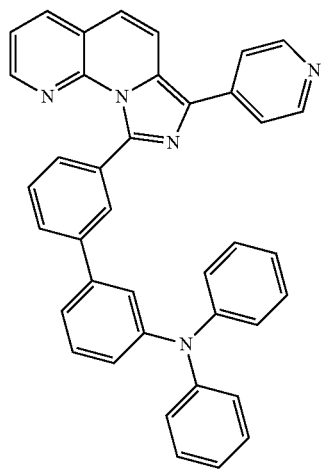
30
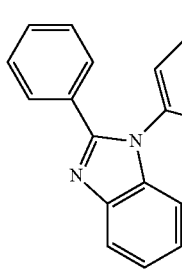
31
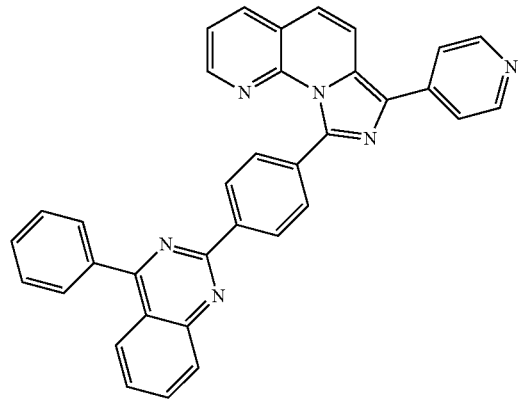
32
-continued
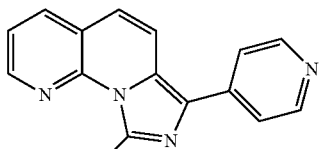
33
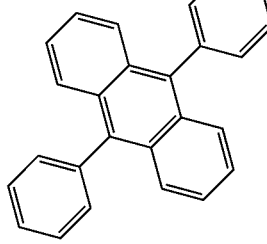
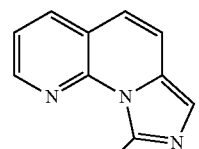
34
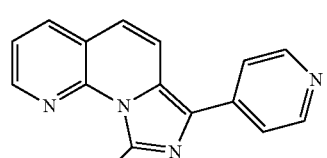
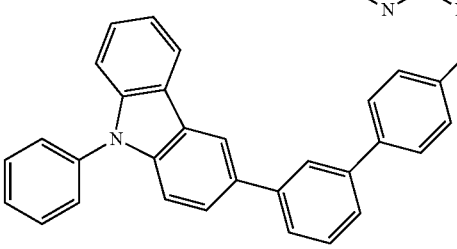
35
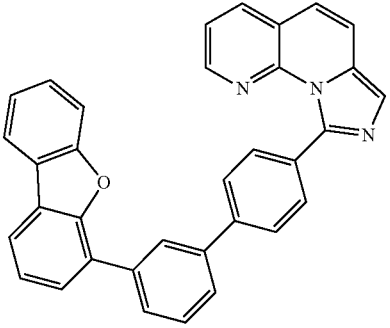
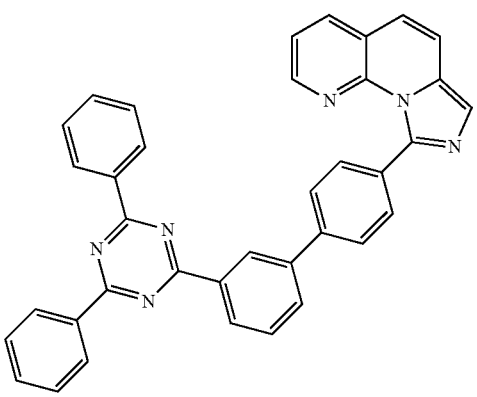
36
The preparation method of the above organic electroluminescent material includes the following steps:
(1) Providing the Compound A,
(2) Under alkaline conditions, reacting the Ar-containing borate or Ar-containing pinacol borate with the Compound A to obtain the compound of Formula (I) by using tetrakistriphenylphosphine palladium as a catalyst.

A:

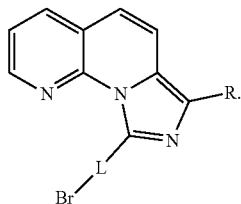

The preparation method of the compound A is as follows:
A) under the function of n-butyllithium, reacting 2-bromo-1,8-dinaphthyridine with R's formiate to obtain Compound B,
B) reacting the Compound B with bromo-L's formaldehyde compound CHO-L-Br to obtain the Compound A.

The R's formiate is R's methyl formiate

The imidazole [1,5-a][1,8]naphthyridine compound of the invention can be applied to the fields of organic electroluminescence devices, solar cells, organic thin film transistors or organic susceptors.

The invention also provides an organic electroluminescence device including an anode, a cathode and an organic layer. The organic layer includes at least one of a light-emitting layer, a hole injection layer, a hole transport layer, an electron injection layer, and an electron transport layer. At least one of the organic layers contains the imidazole [1,5-a][1,8]naphthyridine compound presented by Formula (I).

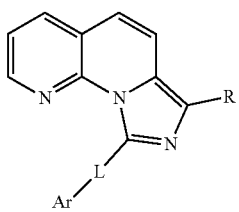

(I)

Where Ar, L and R are defined as mentioned above.

The organic layer is a light-emitting layer and an electron transport layer, or the organic layer is a light-emitting layer, a hole injection layer, a hole transport layer and an electron transport layer, or the organic layer is a light-emitting layer, a hole injection layer, a hole transport layer, an electron transport layer, and an electron injection layer, or the organic layer is a light-emitting layer, a hole transport layer, an electron transport layer, and an electron injection layer, or the organic layer is a light-emitting layer, a hole transport layer, and an electron injection layer.

Preferably, the layer where the imidazole [1,5-a][1,8] naphthyridine compound presented by Formula (I) is contained is a light-emitting layer.

Preferably, the compound containing the imidazole [1,5-a][1,8]naphthyridine presented by Formula (I) is the compounds of Formulas 1-36.

When the compound containing the imidazole [1,5-a][1, 8] naphthyridine presented by Formula (I) is used for manufacturing light-emitting devices, it can be used alone, or also be used in combination with other compounds, or two or more of the compounds in Formula (I) can be simultaneously used.

Preferably, the organic electroluminescent device according to the invention further includes an anode, a hole transport layer, a light emitting layer, an electron transport layer, an electron injection layer and a cathode, wherein the light emitting layer contains the compound having Formula (I), more preferably, the compound contained in the light-emitting layer is the compound having Formula 1-36.

The total thickness of the organic layer in the organic electroluminescent device according to the invention is 1-1000 nm, preferably 50-500 nm.

When the compound having Formula (I) in the invention is applied to organic electroluminescent devices, it can be used in combination with other materials to obtain a blue light, a green light, a yellow light, a red light or a white light.

Each layer of the organic layers in the organic electroluminescent device according to the invention can be prepared by the method such as vacuum vapor deposition, molecular beam vapor deposition, solvent-soluble dip coating, bar coating, or inkjet printing. For metal electrodes, vapor deposition or sputtering method can be adopted for preparation.

Device experiments show that the compound containing imidazole [1,5-a][1,8]naphthyridine presented by Formula (I) in the invention has good thermal stability and high capability of balanced hole/electron transport. The device manufactured by using the organic electroluminescent compound has the advantages such as good electroluminescence efficiency, excellent color purity and long life span.

Figure 1:
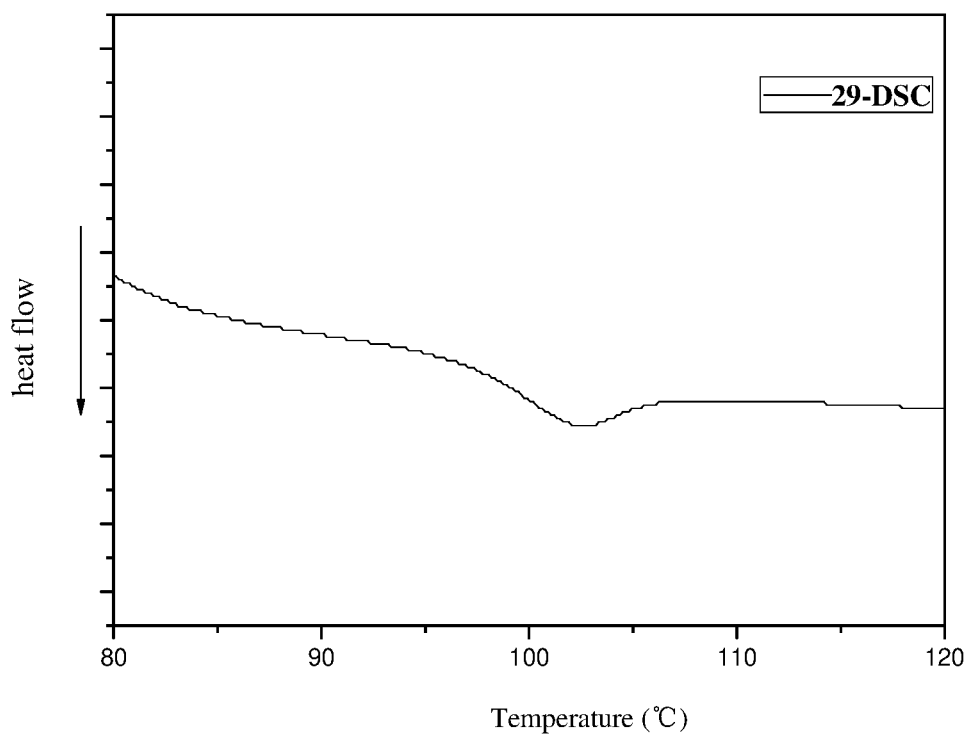
FIG. 1 is the DSC spectrum of Compound 29.

110—glass substrate, 120—anode, 130—hole injection layer, 140—hole transport layer, 150—light emitting layer, 160—electron transport layer, 170—electron injection layer, 180—cathode.

DETAILED DESCRIPTION OF THE PREFERRED EMBODIMENTS

Some example for describing embodiments of the invention are as below. These examples should not be construed as restrictive condition. Unless otherwise mentioned, all percentages are calculated by weight, and all solvent mixture ratios are calculated by volume.

Synthetizing Intermediates

Synthetizing Intermediate 1

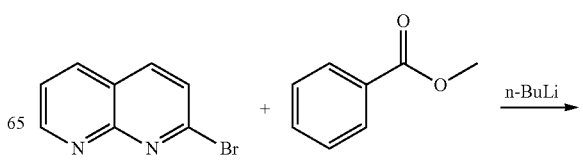

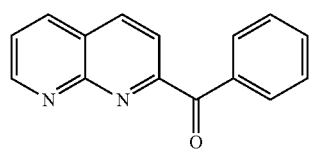

Intermediate 1

2-Bromo-1,8-dinaphthyridine (10 g, 47.84 mmol) and anhydrous THF (100 ml) are put into a three-necked flask, and stirred for 20 minutes at −50° C. under a nitrogen atmosphere, then the hexane solution of n-butyl lithium (2.2 m, 26 ml, 57 mmol) is slowly dropwise added through a constant pressure low liquid funnel. After finished adding, stirring continues while keeping the temperature for half an hour, then the THF solution of methyl benzoate (6.84 g, 50.2 mmol) is added dropwise, subsequently, temperature rises to room temperature, and stirring is carried out overnight. After finished reaction, saturated ammonium chloride solution is used to quench the reaction, after separating out an organic phase and extracting an inorganic phase by ethyl acetate, the organic phase is amalgamated. The product is purified by column chromatography to obtain an intermediate (7.7 g) with yield of 71%.

Synthetizing Intermediate 2

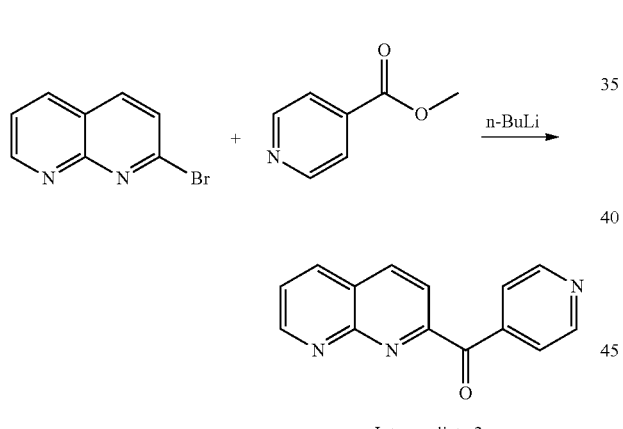

Intermediate 2

The raw material for synthetizing is methyl 4-picolinate, the synthesis method is the same as that of the Intermediate 1, and the yield is 68%.

Synthetizing Intermediate 3

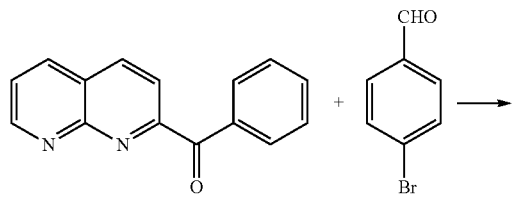

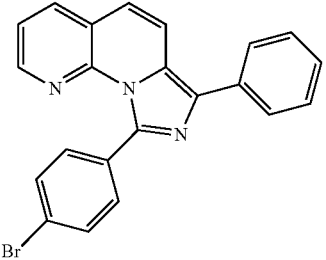

Intermediate 3

The Intermediate 1 (3 g, 12.8 mmol), p-bromobenzaldehyde (2.37 g, 12.8 mmol), ammonium acetate (29.6 g, 0.38 mol) and acetic acid (60 ml) are put into a flask, and heated to 130° C. under a nitrogen atmosphere, and react for 15 hours. After finished reaction, the reaction liquid is cooled, after removing the acetic acid under reduced pressure, and adding water, then extracted by dichloromethane, and an organic phase is collected. After drying and concentrating, a crude product is obtained. The crude product is purified by silica gel column chromatography to obtain an intermediate (3.5 g) with yield of 70%.

Synthetizing Intermediate 4

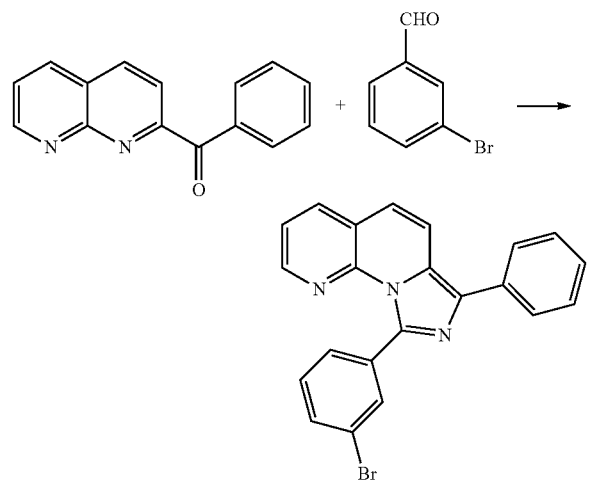

Intermediate 4

The raw material for synthetizing is m-bromobenzaldehyde, the synthesis method is the same as that of the Intermediate 3, and the yield is 65%.

Synthetizing Intermediate 5

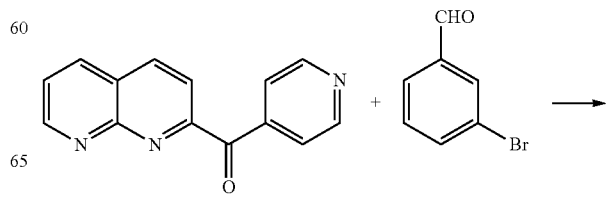

17
-continued

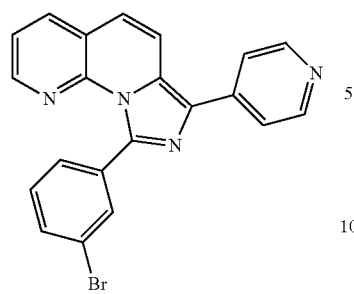

Intermediate 5

The Intermediate 2 (6 g, 25.5 mmol), m-bromobenzaldehyde (4.7 g, 25.5 mmol), ammonium acetate (49 g, 0.64 mol) and acetic acid (100 ml) are put into a flask, and heated to 130° C. under a nitrogen atmosphere, and react for 15 hours. After finished reaction, the reaction liquid is cooled, after removing the acetic acid under reduced pressure, and adding water, then extracted by dichloromethane, and an organic phase is collected. After drying and concentrating, a crude product is obtained. The crude product is purified by silica gel column chromatography to obtain an intermediate (6 g) with yield of 59%.

Example 1—Synthetizing Compound 18

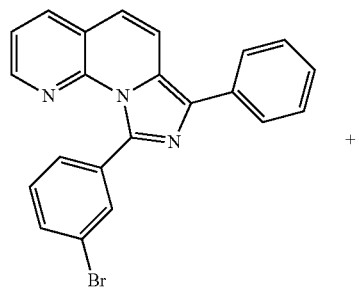

Intermediate 4

18
-continued

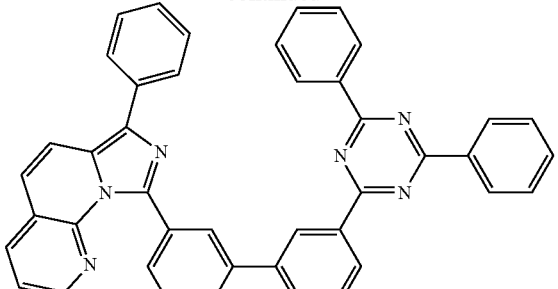

Compound 18

The Intermediate 4 (1 g, 2.5 mmol), 2,4-diphenyl-6-((3-pinacol borate)phenyl)-1,3,5-triazine (1.2 g, 2.75 mmol), tetra(triphenylphosphine)palladium (0.29 g, 0.25 mmol), potassium carbonate (0.86 g, 6.2 mmol) and dioxane/water (10 ml/2 ml) are put into a round bottom flask. The reaction mixture is heated to 110° C. under a nitrogen atmosphere and stirred for 10 hours. After the reaction, it is washed by water, extracted by dichloromethane, and concentrated to obtain a crude product, which is purified by silica gel column chromatography to obtain a compound (1.27 g) with yield of 81%. Ms(ESI): 629.2 (M+1).

Example 2—Synthetizing Compound 21

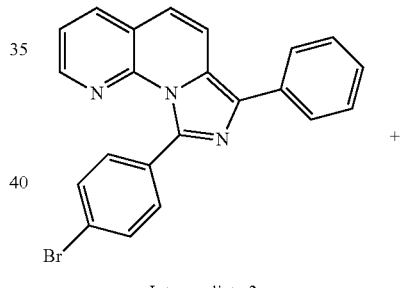

Intermediate 3

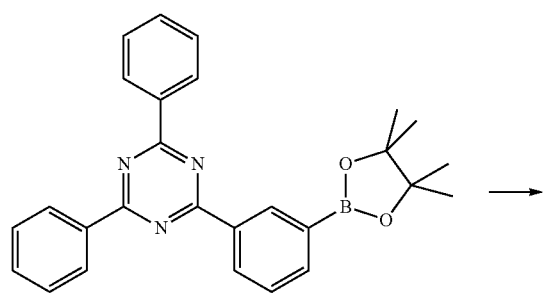

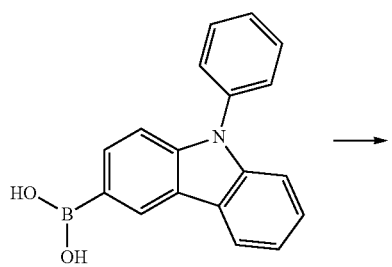

Compound 21

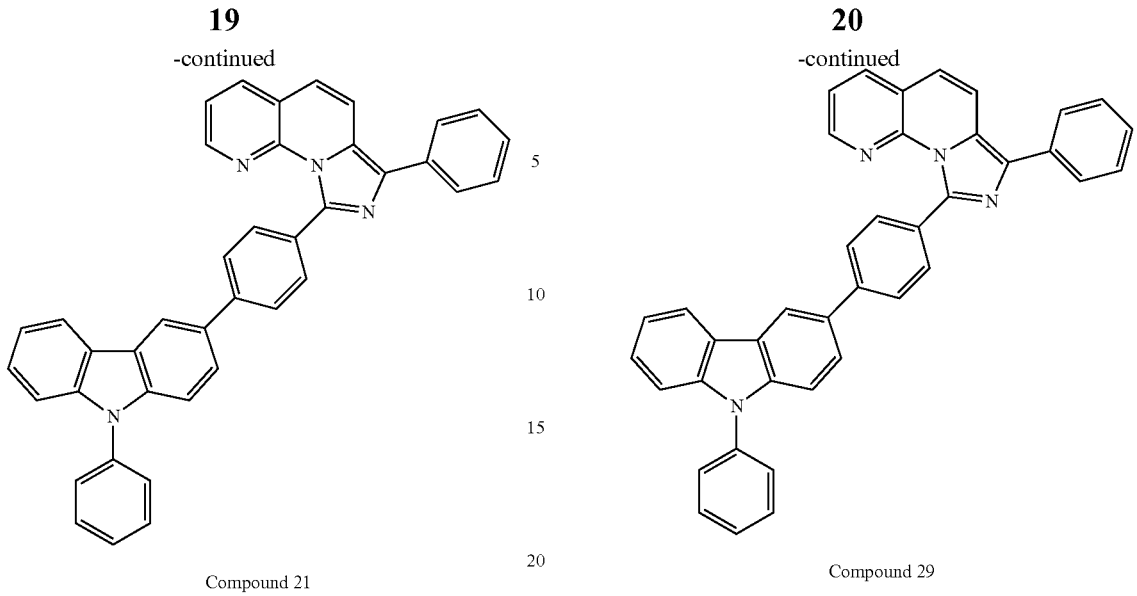

Compound 29

The Intermediate 3 (1 g, 2.5 mmol), N-phenyl-3-carbazoleboronic acid (0.79 g, 2.75 mmol), tetra(triphenylphosphine) palladium (0.29 g, 0.25 mmol), potassium carbonate (0.86 g, 6.2 mmol) and methylbenzene/water (10 ml/2 ml) are put into a round bottom flask. The reaction mixture is heated to 110° C. under a nitrogen atmosphere and stirred for 8 hours. After the reaction, it is washed by water, extracted by dichloromethane, and concentrated to obtain a crude product, which is purified by silica gel column chromatography to obtain a compound (1.04 g) with yield of 74%. Ms(ESI): 563.2 (M+1).

Example 3—Synthetizing Compound 29

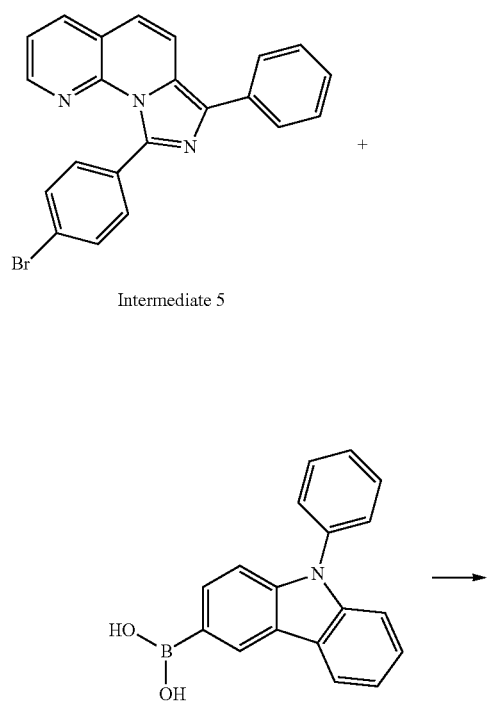

Intermediate 5

The Intermediate 5 (2 g, 5 mmol), (3-(10H-spiro[acridine-9,9'-fluorene]-10-yl)phenyl)boronic acid (2.47 g, 6 mmol), tetra(triphenyl) phosphine) palladium (0.58 g, 0.5 mmol), potassium carbonate (1.7 g, 12.5 mmol) and dioxane/water (20 ml/4 ml) are put into a round bottom flask. The reaction mixture is heated to 110° C. under a nitrogen atmosphere and stirred for 10 hours. After the reaction, it is washed by water, extracted by dichloromethane, and concentrated to obtain a crude product, which is purified by silica gel column chromatography to obtain a compound (3.08 g) with yield of 85%. Ms(ESI): 728.3 (M+1). The glass transition temperature is 99° C. FIG. 1 shows the DSC spectrum of the Compound 29.

Examples 4-6

Preparing an organic electroluminescent device

The compounds in the examples of the invention are used to prepare OLEDs.

First, washing the transparent conductive ITO glass substrate 110 (with an anode 120 on it) sequentially by deionized water, ethanol, acetone, and deionized water, and then treating it with oxygen plasma for 30 seconds.

Then, evaporatively depositing a 5 nm thick hole injection layer 130 (HATCN).

Then, evaporatively depositing a 50 nm thick hole transport layer 140 (TAPC) on the hole injection layer.

Then, evaporatively depositing a 10 nm thick compound of the example doped with 10 wt % Pt-1 as a light-emitting layer 150 on the hole transport layer.

Then, evaporatively depositing a 50 nm thick electron transport layer 160 (TmPyPb) on the light-emitting layer.

Finally, evaporatively depositing a 1 nm thick LiF as the electron injection layer 160 and a 100 nm thick Al as the device cathode 180.

Figure 2:
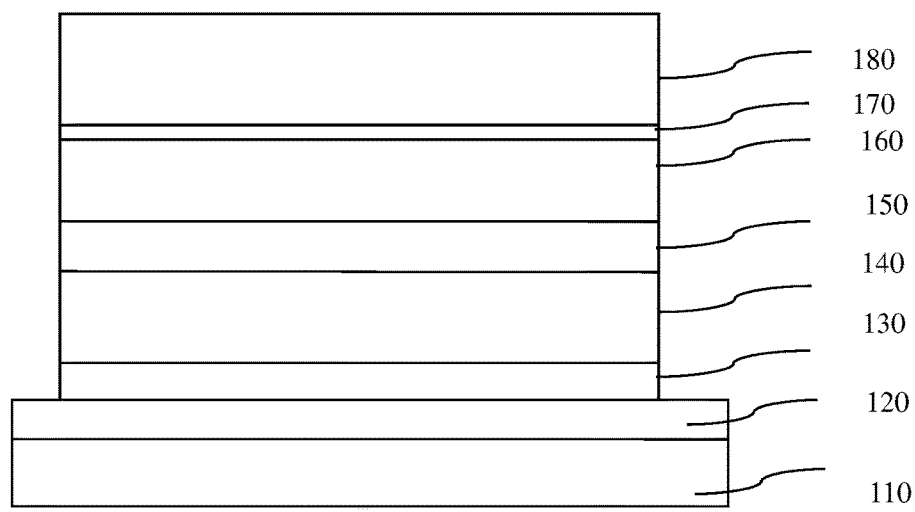
FIG. 2 is the schematic diagram of the organic electroluminescent device.

The prepared device (see FIG. 2 for a schematic diagram) has efficiency measured by a Photo Research PR650 spectrometer at a current density of 1000 cd/m2, as shown in Table 1.

Comparative Example 1

Except replacing the compound of the invention with CBP in the light-emitting layer, everything else is the same as in Example 4.

The prepared device (see FIG. 2 for a schematic diagram) has efficiency measured by a Photo Research PR650 spectrometer at a current density of 1000 cd/m2, as shown in Table 1.

TABLE 1

| Example | Compound | CE (cd/A) | PE (lm/W) at 20 mA/cm² | EQE (%) | CIE (x, y) |
|---|---|---|---|---|---|
| 4 | 18 | 58.7 | 43 | 16.2 | (0.33, 0.62) |
| 5 | 21 | 89.8 | 68.0 | 24.6 | (0.31, 0.64) |
| 6 | 29 | 95.6 | 71.7 | 26.1 | (0.31, 0.64) |
| Comparative Example 1 | CBP | 41.9 | 29.1 | 12.1 | (0.30, 0.65) |

It can be seen from Table 1 that under the same conditions, the efficiency of the organic electroluminescent device manufactured by applying the imidazole [1,5-a][1,8]naphthyridine compound of the invention is higher than that of the comparative example. As mentioned above, the compound of the invention has high stability, and the organic electroluminescent device according to the invention has high efficiency.

The structural Formula (I)n the device is as follows:

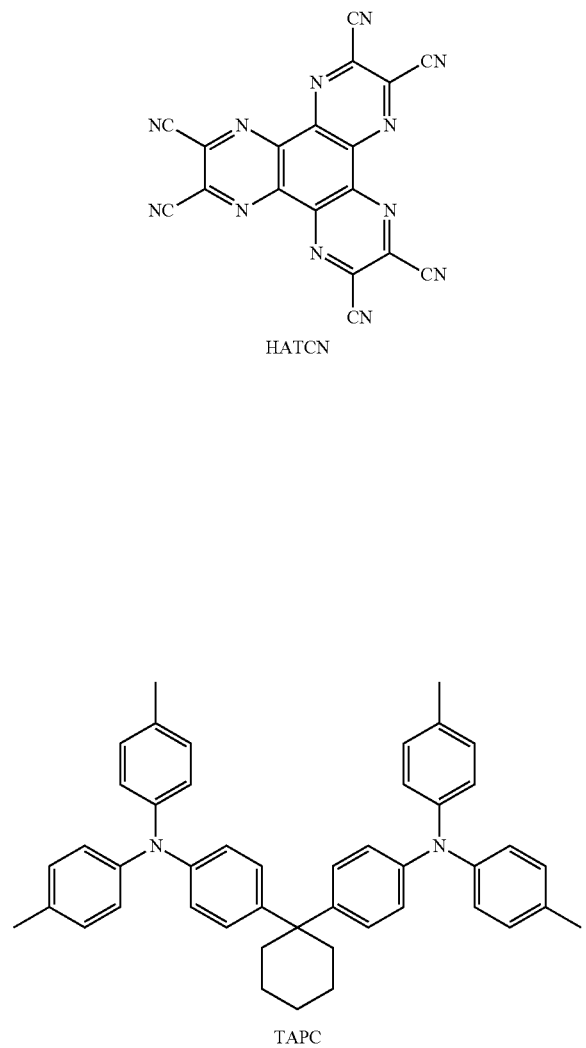

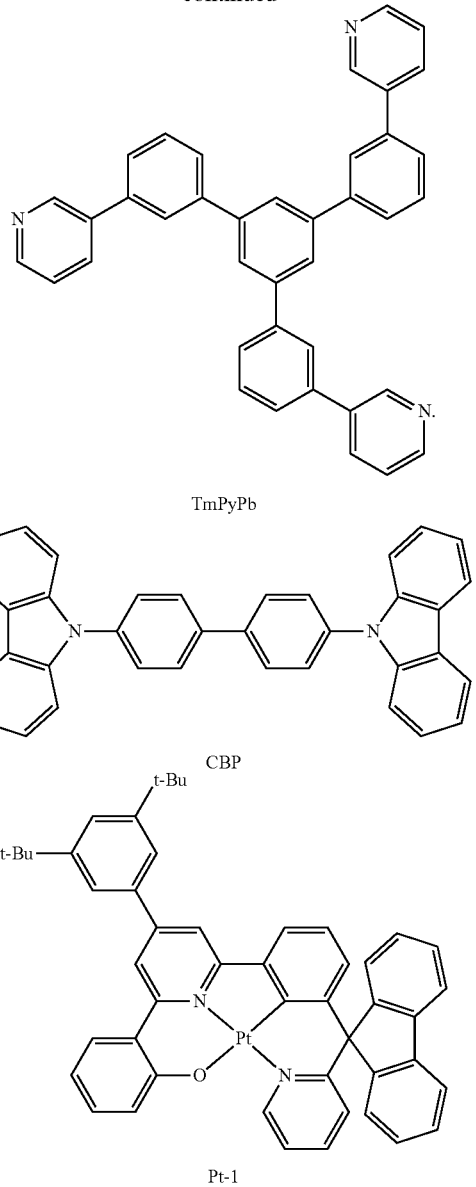

Therefore, a higher device efficiency than a device prepared by CBP can be reached by using the imidazole [1,5-a][1,8] naphthyridine compound of the invention as a subject. Under the same test conditions, the device prepared by CBP at 1000 cd/m², has current efficiency of 41.9 cd/A, power efficiency of 29.1 1 m/W, and external quantum efficiency of 12.1%. However, the devices prepared by using the compounds of the invention's example can achieve effects superior to the above efficiency. In addition, the glass transition temperature Tg of CBP is 62° C., and the compound of the Example 29 in the invention has a higher glass transition temperature Tg (99° C.), as the higher the glass transition temperature is with good morphological stability of the light-emitting layer in the device, the better its application prospect will be, it further meets the requirements of organic light emitting diodes for subject materials.

What is claimed is:

1. An organic electroluminescent material having a chemical structure of Formula (I)

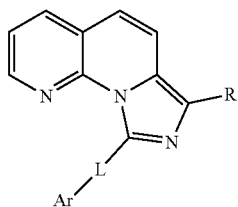

(I)

wherein:
Ar is selected from a C6-C30 substituted or unsubstituted aryl group, a C5-C30 substituted or unsubstituted aryl group having one or more heteroatoms, a N-aryl substituted carbazolyl group, a N-aryl substituted indenocarbazole derivative substituent group, a diarylamino group or a $R_1$-$R_8$ substituted diarylamino group and cyclic derivatives thereof Cy Z is $C(R_9)_2$, $Si(R_9)_2$, O, S, $NR_9$ or $SO_2$, $R_1$-$R_9$ are independently a hydrogen atom, a deuterium atom, halogen, an unsubstituted alkyl group, a halogenated alkyl group, a deuterated alkyl, a cycloalkyl, an unsubstituted aryl, an alkyl-substituted aryl, an alkoxyl group, a cyano group, a carbazolyl group or a diphenylamine group, or $R_1$-$R_9$ independently form a 5-8 membered ring with adjacent groups, Cy:

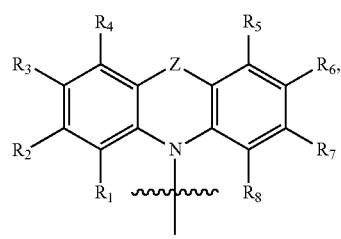

L is selected from a phenylene group, a biphenylene group or a naphthalene group, and R is selected from a hydrogen atom, a deuterium atom, a C6-C10 substituted or unsubstituted aryl group or a C6-C10 heteroaryl group.

2. The organic electroluminescent material according to claim 1, wherein:

Ar is selected from a phenyl group, a naphthyl group, a biphenyl group, a phenanthryl group, an anthracenyl group, an arylanthryl group, a pyrenyl group, a dibenzofuranyl group, a dibenzothienyl group, a benzimidazolyl group, a pyridyl group, a pyrimidinyl group, a quinolyl group, an isoquinolyl group, a triazinyl group, a pyrrolyl group, a furanyl group, a thiazolyl group, a quinazolinyl group, a triazolyl group, a benzothiazolyl group, a benzothiadiazolyl group, a 1,2,4-triazolyl group, a triphenylamino group, an arylcarbazolyl group, a N-aryl substituted carbazolyl group, a diphenylamino group, an acridinyl, a phenoxazinyl or a phenothiaziny, and R is selected from a hydrogen atom, a phenyl group, a naphthyl group or a pyridyl group.

3. The organic electroluminescent material according to claim 2, wherein:

Ar is selected from a phenyl group, a naphthyl group, a biphenyl group, a phenanthryl group, an anthracenyl group, an arylanthryl group, a pyrenyl group, a dibenzofuranyl group, a dibenzothienyl group, a benzimidazolyl group, a pyrimidinyl group, a triazinyl group, a quinazolinyl group, a 1,2,4-triazolyl group, a N-phenyl-carbazole group or an acridinyl.

4. An organic electroluminescent material according to claim 2, comprising one or more of the following compounds:

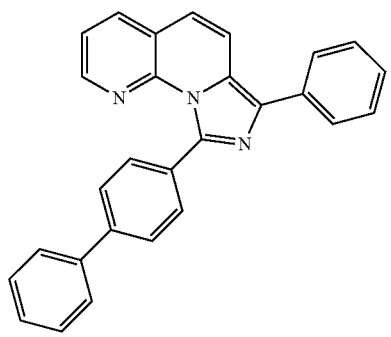

1

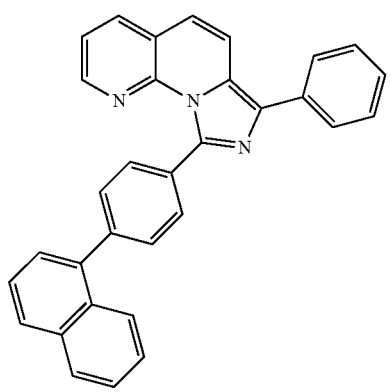

2

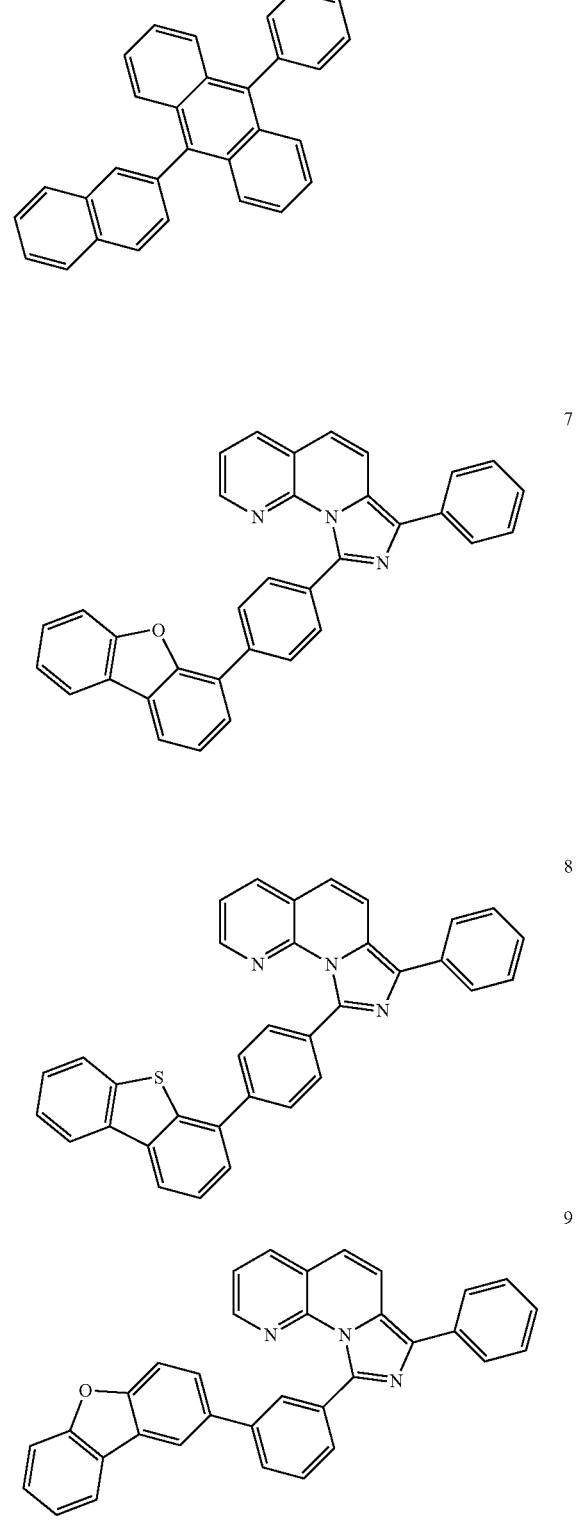

-continued
10
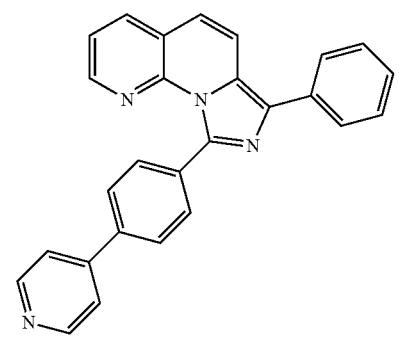
11
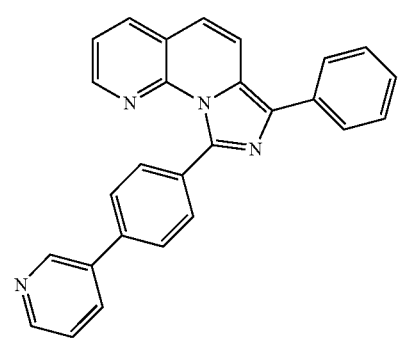
12
13
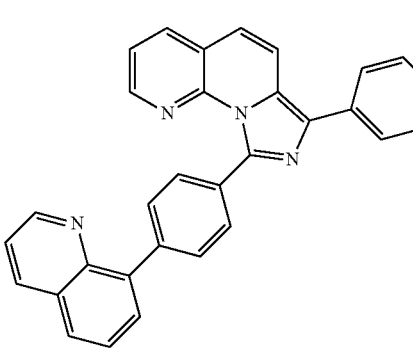
-continued
14
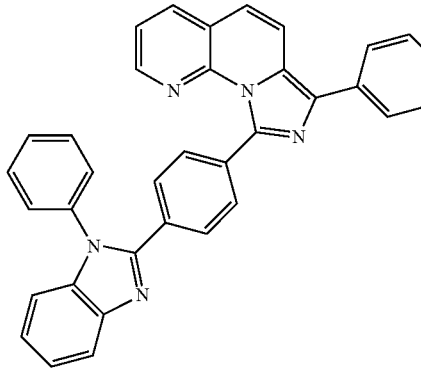
15
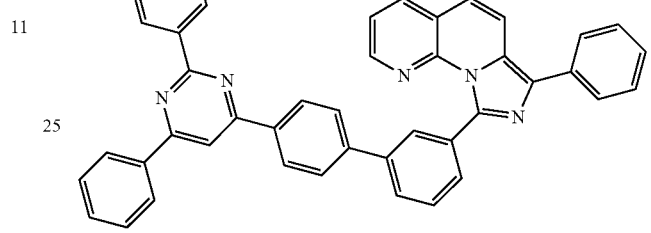
16
17

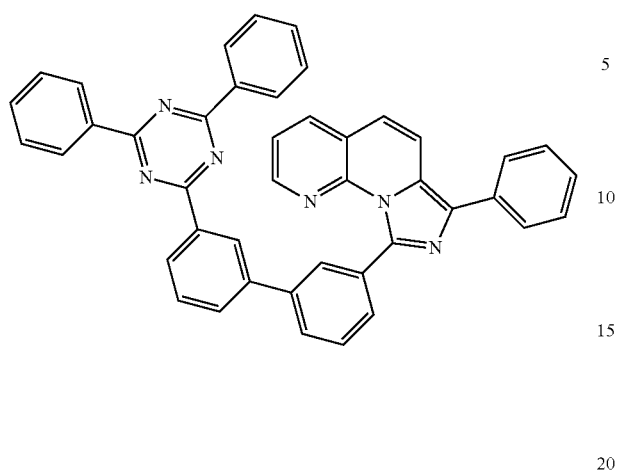
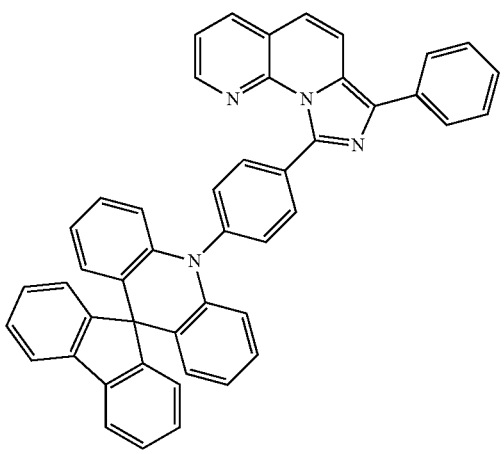
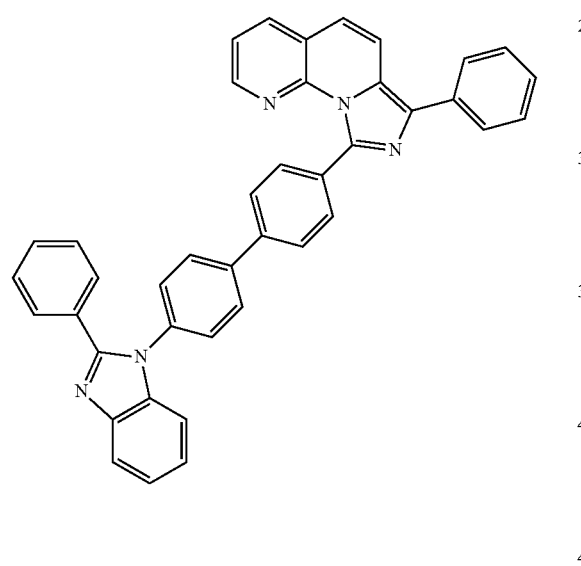
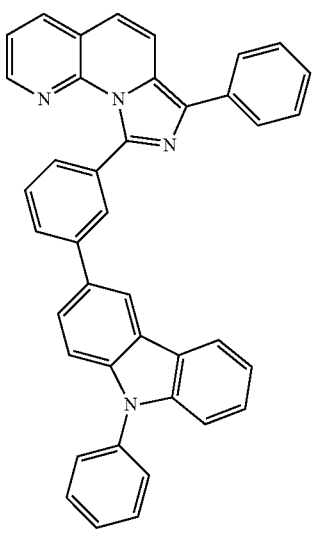
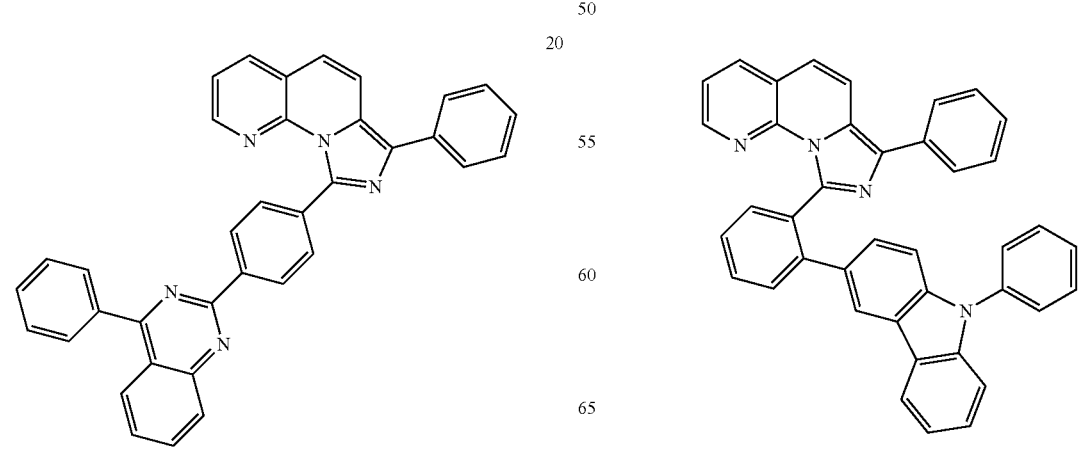

24
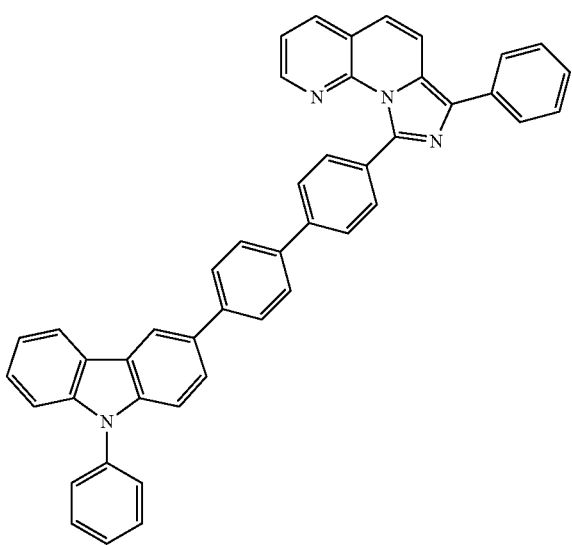
25
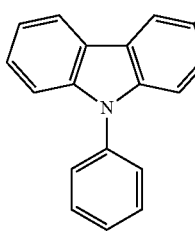
26
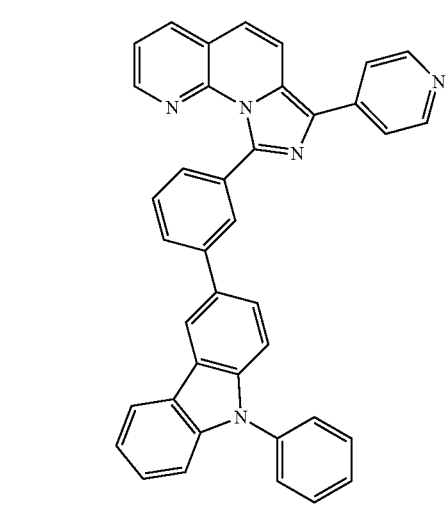
27
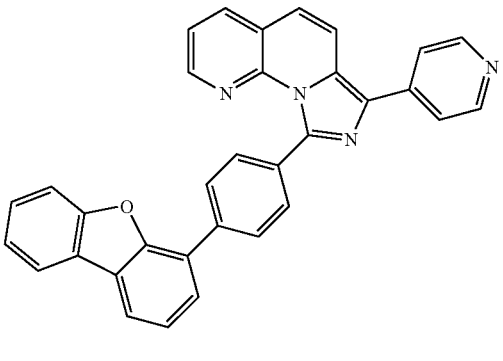
28
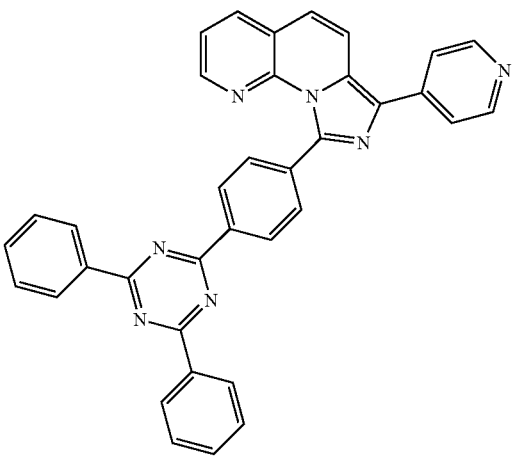
29
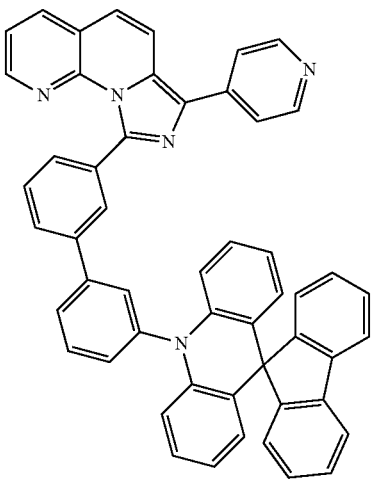

30
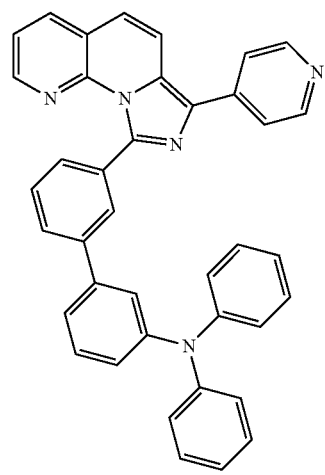
31
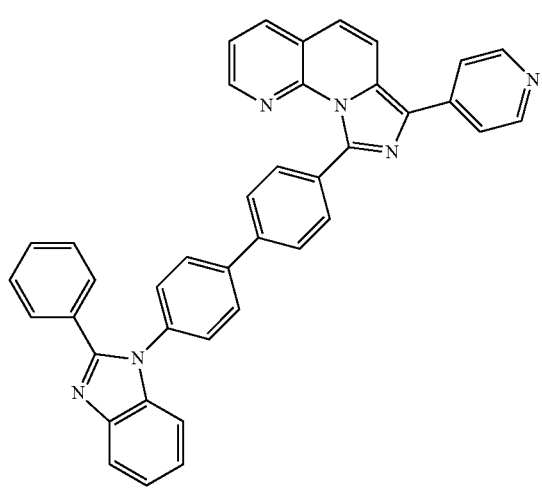
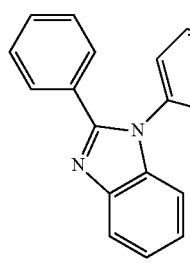
32
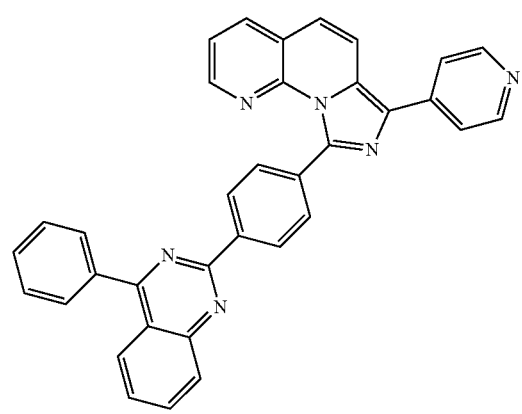
33
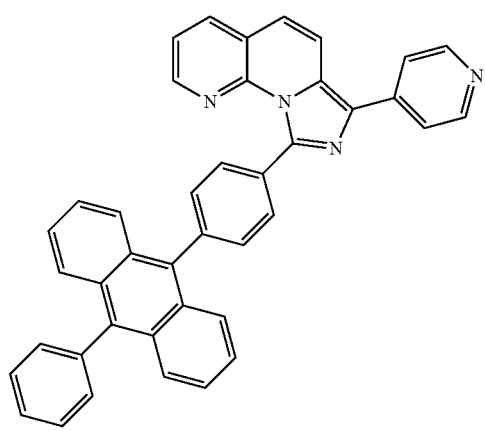
34
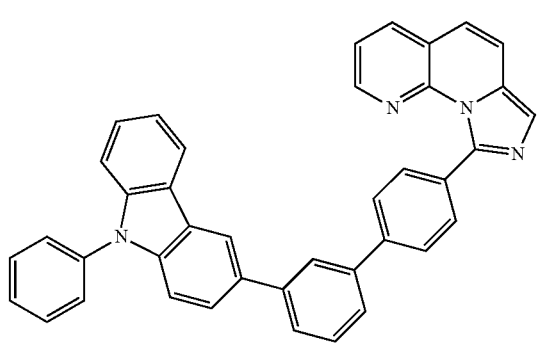
35
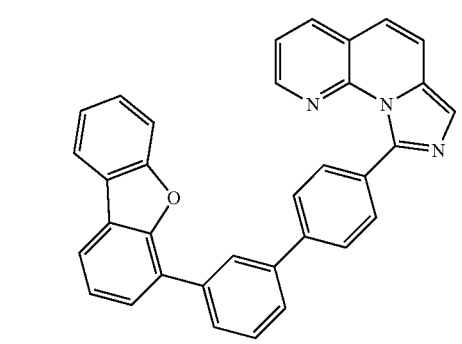
36
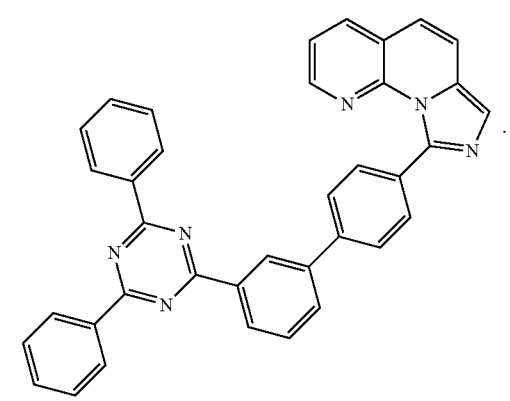

5. An organic electroluminescent material according to claim 4, comprising the following compounds:

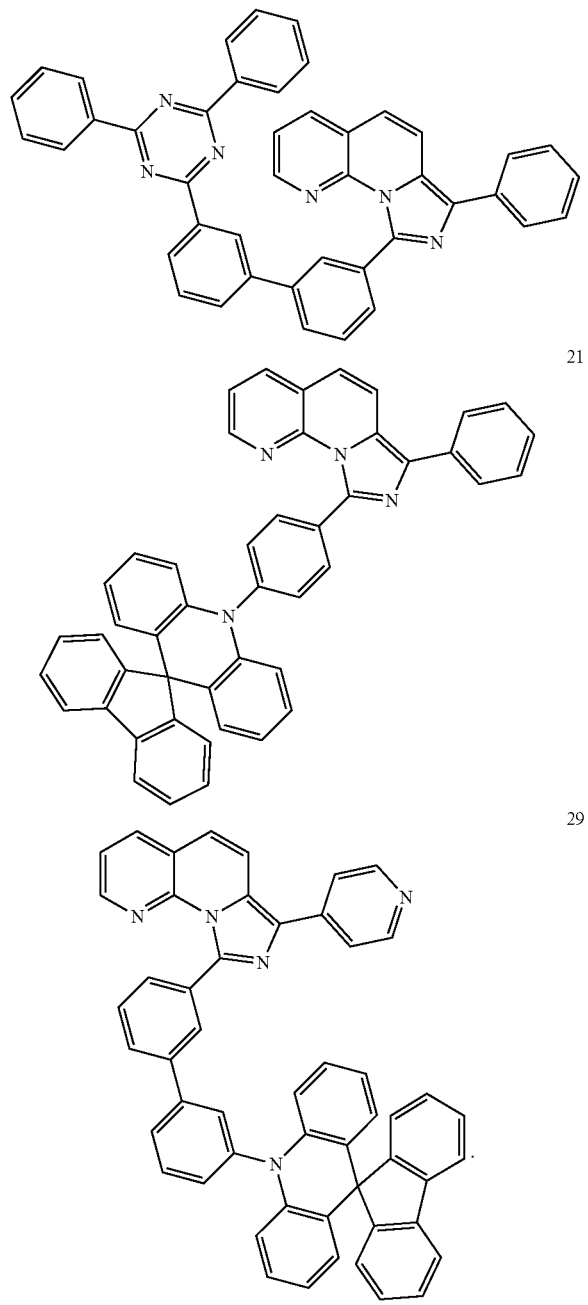

6. An organic electroluminescence device comprising:
an anode,
a cathode, and
an organic layer,
wherein:
said organic layer includes at least one of a light-emitting layer, a hole injection layer, a hole transport layer, an electron injection layer, and an electron transport layer, and
said organic layer contains said organic electroluminescent material according to claim 4.

7. The organic electroluminescent device according to claim 6, wherein the layer in which said organic electroluminescent material is contained is a light-emitting layer.

8. An organic electroluminescence device comprising:
an anode,
a cathode, and
an organic layer,
wherein:
said organic layer includes at least one of a light-emitting layer, a hole injection layer, a hole transport layer, an electron injection layer, and an electron transport layer, and
said organic layer contains said organic electroluminescent material according to claim 2.

9. The organic electroluminescent device according to claim 8, wherein the layer in which said organic electroluminescent material is contained is a light-emitting layer.

10. The organic electroluminescent device according to claim 8, wherein the total thickness of said organic layer is 1-1000 nm, prepared by vacuum vapor deposition, molecular beam vapor deposition, solvent-soluble dip coating, bar coating, or inkjet printing.

11. A preparation method for said organic electroluminescent material according to claim 1, comprising:
S1: providing the Compound A, and
S2: under alkaline conditions, reacting an Ar-containing borate or Ar-containing pinacol borane with the Compound A to obtain the compound of Formula (I) by using tetrakistriphenylphosphine palladium as a catalyst, A:

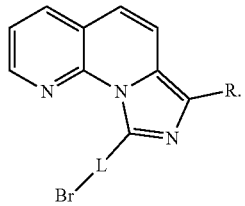

12. The preparation method according to claim 11, wherein the preparation method of said Compound A comprises:
S11: under the function of n-butyllithium, 2-bromo-1,8-dinaphthyridine is reacted with a formate-functional R group-containing compounds to obtain Compound B, and S21: reacting said Compound B with bromo-L's formaldehyde compound CHO-L-Br to obtain said Compound A.

13. The preparation method according to claim 12, wherein said formate-functional R group-containing compound is a methyl formate-functional R group-containing compound.

14. An organic electroluminescence device comprising:
an anode,
a cathode, and
an organic layer,
wherein:
said organic layer includes at least one of a light-emitting layer, a hole injection layer, a hole transport layer, an electron injection layer, and an electron transport layer, and
said organic layer contains said organic electroluminescent material according to claim 1.

15. The organic electroluminescent device according to claim 14, wherein the layer in which said organic electroluminescent material is contained is a light-emitting layer.

16. The organic electroluminescent device according to claim 14, wherein said organic electroluminescent material is used alone, or in combination with other compounds in the light-emitting layer.

17. The organic electroluminescent device according to claim 14, wherein the total thickness of said organic layer is 1-1000 nm, prepared by vacuum vapor deposition, molecular beam vapor deposition, solvent-soluble dip coating, bar coating, or inkjet printing.

* * * * *